(12) United States Patent
Jones (10) Patent No.: US 9,322,893 B2
(45) Date of Patent: Apr. 26, 2016

(54) METHODS OF DISTINGUISHING BETWEEN GLUTAMINE FORMED BY CATAPLEROSIS OR PROTEOLYSIS

(75) Inventor: John Griffith Jones, Coimbra (PT)

(73) Assignee: BIOCANT-ASSOCIAÇÃO DE TRANSFERÊNCIA DE TECNOLOGIA, Cantanhede (PT)

( * ) Notice: Subject to any disclaimer, the term of this patent is extended or adjusted under 35 U.S.C. 154(b) by 594 days.

(21) Appl. No.: 12/993,934

(22) PCT Filed: May 22, 2009

(86) PCT No.: PCT/GB2009/001282
§ 371 (c)(1),
(2), (4) Date: Nov. 22, 2010

(87) PCT Pub. No.: WO2009/141619
PCT Pub. Date: Nov. 26, 2009

(65) Prior Publication Data
US 2011/0079093 A1   Apr. 7, 2011

(30) Foreign Application Priority Data

May 23, 2008 (GB) .................................. 0809445.0
May 21, 2009 (PT) ........................................ 104585

(51) Int. Cl.
G01N 24/08 (2006.01)
G01R 33/465 (2006.01)
G01N 33/60 (2006.01)
G01N 33/68 (2006.01)
G01N 33/94 (2006.01)

(52) U.S. Cl.
CPC .............. *G01R 33/465* (2013.01); *G01N 33/60* (2013.01); *G01N 33/6812* (2013.01); *G01N 33/6893* (2013.01); *G01N 33/94* (2013.01); *G01N 24/08* (2013.01); *G01N 2500/00* (2013.01); *G01N 2800/04* (2013.01); *Y10T 436/24* (2015.01)

(58) Field of Classification Search
CPC .. G01R 33/465; G01R 2800/04; G01R 24/08; G01R 33/6893; Y10T 436/24
See application file for complete search history.

(56) References Cited

PUBLICATIONS

Kuhn et al. (1999) "Determination of glutamine in muscle protein facilitates accurate assessment of proteolysis and de novo synthesis-derived endogenous glutamine production," Am J Clin Nutr; 70:484-489.
Hankard et al. (2000) "Role of glucose in the regulation of glutamine metabolism in health and in type 1 insulin-dependent diabetes," Am J Physiol Endocrinol Metab, 279: E608-E613.

(Continued)

*Primary Examiner* — Yelena G Gakh
*Assistant Examiner* — Michelle Adams
(74) *Attorney, Agent, or Firm* — Swanson & Bratschun, L.L.C.

(57) ABSTRACT

The present invention relates to methods of distinguishing between glutamine formed by cataplerosis or proteolysis. Sample from a subject may be assayed for deuteriated glutamine (following administration of deuteriated water ($^2H_2O$) and an agent that promotes excretion of glutamine from the subject). The methods are useful in clinical settings (e.g. to test whether or not patients are suffering from proteolysis or whether athletes are abusing anabolic drugs); and may be adapted for screening test compounds for cataplerotic or proteolytic activity.

15 Claims, 4 Drawing Sheets

(56) References Cited

PUBLICATIONS

Chapa et al. (2000) "Metabolism of ($1$-$^{13}$C) glucose and ($2$-$^{13}$C, $2$-$^{2}$H$_3$) acetate in the neuronal and glial compartments of the adult rat brain as detected by {$^{13}$C, $^{2}$H} NMR spectroscopy," Neurochemistry International, 37:217-228.

Jones et al. (2001) "An integrated $^{2}$H and $^{13}$C NMR study of gluconeogenesis and TCA cycle flux in humans," Am J Physiol Endocrinol Metab 281:E848-E856.

Perdigoto et al. (2003) "Integration of [U-$^{13}$C]glucose and $^{2}$H$_2$O for quantification of hepatic glucose production and gluconeogenesis," NMR in Biomedicine, 16:189-198.

Kadrofske et al. (2006) "Effect of intravenous amino acids on glutamine and protein kinetics in low-birth-weight preterm infants during the immediate neonatal period," Am J Physiol Endocrinol Metab 290: E622-E630.

Hankard et al. (Oct. 1995) "Response of glutamine metabolism to exogenous glutamine in humans," The American Journal of Physiology, 269:E663-E670.

Garcia-Martin et al. (Mar. 8, 2002) "Hydrogen Turnover and Subcellular Compartmentation of Hepatic [2-$^{13}$C]Glutamate and [3-$^{13}$C]Aspartate as Detected by $^{13}$C NMR," The Journal of Biological Chemistry, 277(10): 7799-7807.

Le Bacquer et al. (2007) "Acute depletion of plasma glutamine increases leucine oxidation in prednisone-treated humans," Clinical Nutrition 26:231-238.

International Search Report issued in PCT/GB2009/001282, mailed Aug. 17, 2009.

Written Opinion issued in PCT/GB2009/001282, Nov. 23, 2010.

International Preliminary Report on Patentability issued in PCT/GB2009/001282.

METHODS OF DISTINGUISHING BETWEEN GLUTAMINE FORMED BY CATAPLEROSIS OR PROTEOLYSIS

RELATED APPLICATIONS

This application is a 35 U.S.C. §371 national phase application of PCT/GB2009/001282, filed May 22, 2009 (WO 2009/141619), entitled "Methods of Distinguishing Between Glutamine Formed by Cataplerosis or Proteolysis". PCT/GB2009/001282 claims priority to GB 0809445.0, filed May 23, 2008 and PT 104585, filed May 21, 2009. Each of these applications is incorporated herein by reference in its entirety.

FIELD OF THE INVENTION

The present invention concerns an assay for distinguishing between the origins of Glutamine in the human or animal body. The assay is particularly suited for distinguishing between cataplerotic and proteolytic sources of hepatic glutamine.

BACKGROUND

Glutamine is an abundant non-essential amino acid that is highly involved in carbon and nitrogen transfer between different organs and tissues. Skeletal muscle is the principal source of whole body glutamine production, accounting for 50-70% of the glutamine rate of appearance ($R_a$). The glutamine carbon skeleton is utilized by the gut as an energy source and by the liver as a gluconeogenic precursor. Thermodynamically, glutamine is a potent gluconeogenic amino acid since its conversion to sugar phosphates is accompanied by a net gain of ATP and reducing equivalents. There is evidence that glutamine derived from peripheral tissues is a significant source of carbon for hepatic gluconeogenesis. Therefore, alterations in whole body glutamine production may have a significant effect on gluconeogenic activity and hepatic glucose metabolism.

Glutamine can be derived from both metabolic and proteolytic sources hence its $R_a$ may be influenced by changes in peripheral metabolic activity or in whole-body protein kinetics. These could include the balance between whole-body protein anabolism and catabolism as well as the intermediary metabolic flux activities of various peripheral tissues.

Skeletal muscle has a relatively large pool of free glutamine that is in rapid turnover and is derived from both metabolic and proteolytic activities. The glutamine content of alkali-soluble muscle protein is about 4%, hence protein breakdown provides a direct source of glutamine. In addition, glutamine can be synthesized from other amino acids that are released during proteolysis, including proline, histidine, asparagine and glutamate. Of these precursors, glutamate is quantitatively the most important since its abundance in skeletal muscle protein is ~4 fold higher than that of glutamine. Consequently, each equivalent of glutamine that is directly released by skeletal muscle proteolysis is accompanied by four of glutamate which can be potentially converted to glutamine. Glutamine can also be derived from the pool of Krebs cycle metabolites via α-ketoglutarate and glutamate. Net glutamine production from this source requires that the α-ketoglutarate that is lost from the Krebs cycle be balanced by anaplerotic inflow into the cycle. In skeletal muscle, activities of pyruvate carboxylase and malic enzyme allow the anaplerotic utilization of pyruvate. Significant levels of anaplerotic flux have been reported in rat skeletal muscle by $^{13}C$ tracers.

There is a long felt medical need for a clinician to be able to identify the sources of whole body glutamine carbons for hepatic gluconeogenic activity. Critical illness is characterized by a loss of lean body mass (muscle wastage) hence there is potential for an increased generation of glutamine from protein breakdown. This setting is also characterized by hyperglycemia and elevated rates of hepatic gluconeogenesis. Given that glutamine may be a significant contributor to hepatic gluconeogenesis in healthy subjects an increased availability of hepatic glutamine during illness could contribute to elevated hepatic gluconeogenic fluxes. However, to date, it has not been possible to detect to what extent whole-body protein breakdown and cataplerotic fluxes contribute to the hepatic glutamine pool. Current methods can estimate the contribution of glutamine released directly from protein breakdown to whole body glutamine $R_a$. However, to the extent that glutamine is synthesized from other amino acids released during protein breakdown (notably glutamate), the prior art methods substantially underestimate the overall contribution of protein degradation to the hepatic glutamine pool and are not useful for early detection of muscle wastage.

It is therefore an object of the present invention to obviate the disadvantages associated with the prior art and provide improved methods for distinguishing between the origins of the carbon skeletons of hepatic glutamine.

SUMMARY

According to a first aspect of the present invention there is provided a method of distinguishing between glutamine formed by cataplerosis or proteolysis in a subject comprising assaying a bodily sample from the subject for deuteriated glutamine;

wherein the bodily sample is from a subject that has had deuteriated water ($^2H_2O$) administered to it and has been treated with an agent that promotes excretion of glutamine from the subject; and wherein the presence of deuteriated glutamine indicates the proportions of glutamine in the bodily sample formed from cataplerosis and proteolysis According to a second aspect of the present invention there is provided a method of distinguishing between glutamine formed by cataplerosis or proteolysis in a subject comprising:
 (a) administering deuteriated water ($^2H_2O$) to the subject;
 (b) treating the subject with an agent that promotes excretion of glutamine from the subject;
 (c) taking a bodily sample from the subject; and
 (d) testing the bodily sample for the presence of deuteriated glutamine;

wherein the presence of deuteriated glutamine, or a deuteriated derivative thereof, indicates the proportions of glutamine in the bodily sample formed from cataplerosis and proteolysis.

By the term "cataplerosis" we mean the reactions responsible for removal of intermediates from the Krebs cycle. There are several cataplerotic enzymes; these include PEPCK, aspartate aminotransferase, and glutamate dehydrogenase. In the context of the present invention, glutamate dehydrogenase is responsible for the conversion of α-ketoglutarate, a Krebs cycle intermediate, to glutamate. Glutamate in turn can be converted in the liver to Glutamine.

By the term "catapleroetic glutamine" we mean glutamine that has derived from the Krebs cycle (from, in turn, glutamate and α-ketoglutarate). Glutamine derived by cataplerosis may have a hydrogen atom at positions 2, 3 or 4 (see FIG. 1) that is derived from body water. Furthermore the hydrogen at this position may be turned-over more frequently than the equivalent hydrogen in glutamine derived from proteolysis.

By the term "proteolytic glutamine" we mean glutamine that, either directly or indirectly, is derived from amino acids that are liberated following the breakdown of proteins.

The present invention is based on a hypothesis that was developed and tested when the inventors realized a number of points could contribute to devising an improved method of measuring glutamine production.

First, they realized that whole-body cataplerotic and proteolytic contributions to glutamine (primarily produced in the liver) may be quantified by analysing glutamine $^2$H-enrichment following $^2$H$_2$O consumption. When body water is enriched with $^2$H$_2$O, free amino acids that are in exchange with pyruvate and Krebs cycle metabolites become rapidly enriched with $^2$H. Amino acids that are released from protein will not be significantly enriched with $^2$H during this time due to the much smaller fractional turnover rate of protein. Glutamate that is derived from the Krebs cycle via cataplerosis will have predictable $^2$H-enrichment levels in specific sites reflecting the participation of water hydrogens in the various steps of the Krebs cycle and during amination of α-ketoglutarate (see FIG. 1). Since the incorporation of $^2$H is preserved during the conversion of glutamate to glutamine, the $^2$H-enrichment level of glutamine reflects the cataplerotic contribution of carbon skeletons to the glutamine pool. The extent to which this enrichment is diluted relative to that of body water is a measure of the contribution of glutamine molecules whose carbon skeletons are derived from protein breakdown.

Second, the inventors realized that it would be possible to measure $^2$H-enrichment of glutamine in a non-invasive way. This may be achieved by combining glutamine with an agent that promotes excretion of the glutamine from the body (e.g. in the urine). It will be appreciated that $^2$H-enrichment of glutamine carbon skeletons will be preserved in the glutamine moiety linked to the agent.

Third, the inventors established that cataplerotic glutamine (enriched in $^2$H) may be distinguished from glutamine derived from proteolysis (without $^2$H enrichment) by examining the molecules using a suitable test system such as Nuclear Magnetic Resonance (NMR) or Mass Spectroscopy.

It will therefore be appreciated that, according to the methods of the invention, that a high proportion (e.g. compared to a standard average or control) of deuteriated glutamine in a sample suggests cataplerosis. Furthermore a low proportion (e.g. compared to a standard average or control) of deuteriated glutamine in a sample suggests proteolysis.

The subject may be any organism in which glutamine may be synthesized in the body by cataplerosis and proteolysis. It is preferred that the subject is a mammal. The mammal may be an animal of veterinary importance or of scientific interest. For instance the subject may be a mammal selected from the group comprising horses, cattle, pigs, sheep, primates, cats, dogs, rats, mice or rabbits. It is most preferred that the subject is a human being.

The methods of the invention can be particularly useful when a researcher wishes to use a subject to screen whether or not a test compound promotes proteolysis or cataplerosis. A bodily sample can be taken from a subject treated with such as test compound, deuteriated water and an agent that promotes excretion of glutamine (as described above). A decrease in the proportion of deuteriated glutamine in a subject, when compared to a control, would suggest that more glutamine in the sample is derived from proteolysis and suggest that the test compound causes proteolysis. Conversely an increase in the proportion of deuteriated glutamine (i.e. cataplerotic glutamine) in a subject would suggest that a test compound reduces protein breakdown and may be anabolic. It will be appreciated that this represents an important feature of the invention and the methods of the first and second aspects of the invention can therefore be adapted for use as a screen for use by the pharmaceutical industry when developing new drugs. Such a screen may also be used to test whether or not athletes are utilizing substances that are banned in their sport.

Therefore according to a third aspect of the invention there is provided a method of screening a compound to establish whether the compound is proteolytic or anabolic comprising assaying a bodily sample from a subject for deuteriated glutamine;

wherein the bodily sample is from a subject that has had deuteriated water ($^2$H$_2$O) administered to it, has been treated with an agent that promotes excretion of glutamine from the subject, and been treated with the compound; and wherein, when compared to a control, an increase in the proportion of deuteriated glutamine indicates that the compound is anabolic or reduces proteolysis and a decrease in the proportion of deuteriated glutamine indicates that the compound promotes proteolysis.

According to a fourth aspect of the present invention there is provided a method of screening a compound to establish whether the compound is proteolytic or anabolic comprising:
 (a) treating a subject with the compound;
 (b) administering deuteriated water ($^2$H$_2$O) to the subject;
 (c) treating the subject with an agent that promotes excretion of glutamine from the subject;
 (d) taking a bodily sample from the subject; and
 (e) testing the bodily sample for the presence of deuteriated glutamine;

wherein, when compared to a control, an increase in the proportion of deuteriated glutamine indicates that the compound is anabolic or reduces proteolysis and a decrease in the proportion of deuteriated glutamine indicates that the compound promotes proteolysis.

The bodily sample according to any aspect of the invention may be any sample in which glutamine, or a conjugate of glutamine with the agent, is excreted. For instance the sample may be sweat or tears. However it is most preferred that the bodily sample is a urine sample.

It will be appreciated that $^2$H$_2$O may be administered to the subjects used in any of the methods of the invention by any means that will allow the $^2$H$_2$O to reach the liver of the subject (where most metabolism of glutamine occurs). The $^2$H$_2$O may be administered in such a way that it is delivered systemically. For instance, the $^2$H$_2$O may be administered by means of an intravenous drip. However it is preferred that the $^2$H$_2$O is ingested. A subject should ideally start to ingest $^2$H$_2$O at least 2 hours before a sample is taken. For instance the subject may start to ingest $^2$H$_2$O 24 hours or more before the bodily sample is taken. Preferably the subject starts ingesting $^2$H$_2$O 16 hours before the sample is taken and more preferably starts about 8 hours before the sample is taken.

In a preferred embodiment it may be intended to collect bodily samples from a subject in the morning (e.g. at 09:00). When this is the case, a subject may start to ingest $^2$H$_2$O the night before. Ideally the subject should also fast (e.g. from 20:00 following a standard dinner/feed). During the night, each subject should drink between 1.0-10.0 g/kg body-water of $^2$H$_2$O and preferably about 5.0 g/kg body-water of $^2$H$_2$O.

When the subject is a human, the $^2$H$_2$O may be administered as a solution (e.g. about 35% $^2$H$_2$O) in non-carbonated water (350 ml total volume). This solution may be divided into 2 equal portions. When samples are to be taken at 09:00, the first portion may be given at 01:00 and the second portion given at 03:00. For the remainder of the study, the subject may drink water containing 0.5% $^2H_2O$ to maintain body water enrichment.

Under some circumstances the methods of the invention may be adapted such that the need for treatment with an agent that promotes excretion of glutamine is obviated. For instance, the test for deuteriated glutamine may be sensitive enough to detect free glutamine that is excreted from the body of a mammal. However there is normally limited excretion of free glutamine and it is generally preferred that an agent that promotes excretion of glutamine is utilised. The agent may be any compound that will react with, bind to, or conjugate with glutamine in such a way that it will promote excretion of glutamine from the body. When the bodily sample is urine it is preferred that the agent comprises a phenylacetyl group and reacts with glutamine to form a Phenylacetylglutamine (PAGN). Preferred agents include aspartame, sodium phenylacetate or sodium phenylbutyrate which can react with glutamine to form a PAGN. It will be appreciated that $^2H$-enriched glutamine (formed by cataplerosis) is preserved in the glutamine moiety of the PAGN. The PAGN may then be isolated from the body in urine and the urine sample tested according to the methods of the invention.

The dose and timing of the treatment with the agent will depend on the specific agent chosen; how it is formulated; its known rate of absorption into the body; and clearance from the body. When the agent is aspartame, sodium phenylacetate or sodium phenylbutyrate it is preferred that it is formulated for oral ingestion. For instance the agent may formulated as a tablet or as a solution to be drunk. In a preferred embodiment the agent is encapsulated in gelatin.

The agent may be ingested 0.5-8 hours before a sample is taken and more preferably about 1-4 hours before the sample is taken. By way of example a gelatin encapsulated agent comprising a phenylacetyl group may be ingested 2 hours before a urine sample is taken. For instance, if urine samples are due to be collected from 09:00, then at 07:00 a human subject may ingest a gelatin capsule containing 50-500 mgs and preferably about 300 mg, of phenylbutyric acid.

It will be appreciated that the $^2H_2O$ and the agent may be given to a subject separately. Alternatively they may be combined in a single aqueous solution in order that the test subject may conveniently ingest a single solution. Alternatively a solution containing $^2H_2O$ may be utilized to help swallow a tablet or gelatin capsule comprising the agent.

The dose and timing of the treatment with test compounds according to the third or fourth aspects of the invention will depend on the nature of the specific compound being tested; how it is formulated; its known rate of absorption into the body; and clearance from the body.

The solution(s) containing the $^2H_2O$ and/or agent and/or test compound may also contain flavourings and the like to make such solutions more palatable.

The bodily sample may be suitable for immediate assay. However, depending on the test procedure used, the bodily sample may need to be processed. For instance the sample may need to be diluted or the glutamine content concentrated to make it suitable for testing. It may also be necessary to free glutamine from the moiety (e.g. a phenylacetyl group) that has promoted excretion of the glutamine from the subject. Some of the procedures utilized to free glutamine may result in the deamination of glutamine to generate glutamate. It will be appreciated that glutamine and glutamate share the same carbon backbone and an analysis of $^2H$ on either glutamine or glutamate will be equally useful for discriminating between cataplerotic glutamine and proteolytic glutamine.

The bodily sample may be tested in a number of ways. For instance, Mass Spectrometry may be used to analyze the glutamine (or glutamate) content of the sample. Conventional Mass Spectrometry techniques may be used.

It is preferred that the methods of the invention involve testing the samples by NMR analysis and more preferred that $^2H$ NMR techniques are employed.

Analysis of low levels of $^2H$-enrichments by NMR requires the recovery of ~0.1-0.2 mmol of analyte. The inventors have found that sufficient analyte is obtained in a urine sample when a single capsule containing 50-500 mgs of an agent according to the invention is ingested and followed by urine collection for about 2-4 hours afterwards. For example a gelatin capsule containing 0.3-0.5 grams of phenylbutyric acid is sufficient to produce enough analyte for NMR analysis of urine from a human subject which is collected for about 2-4 hours after the capsule has been consumed.

Figure 3:
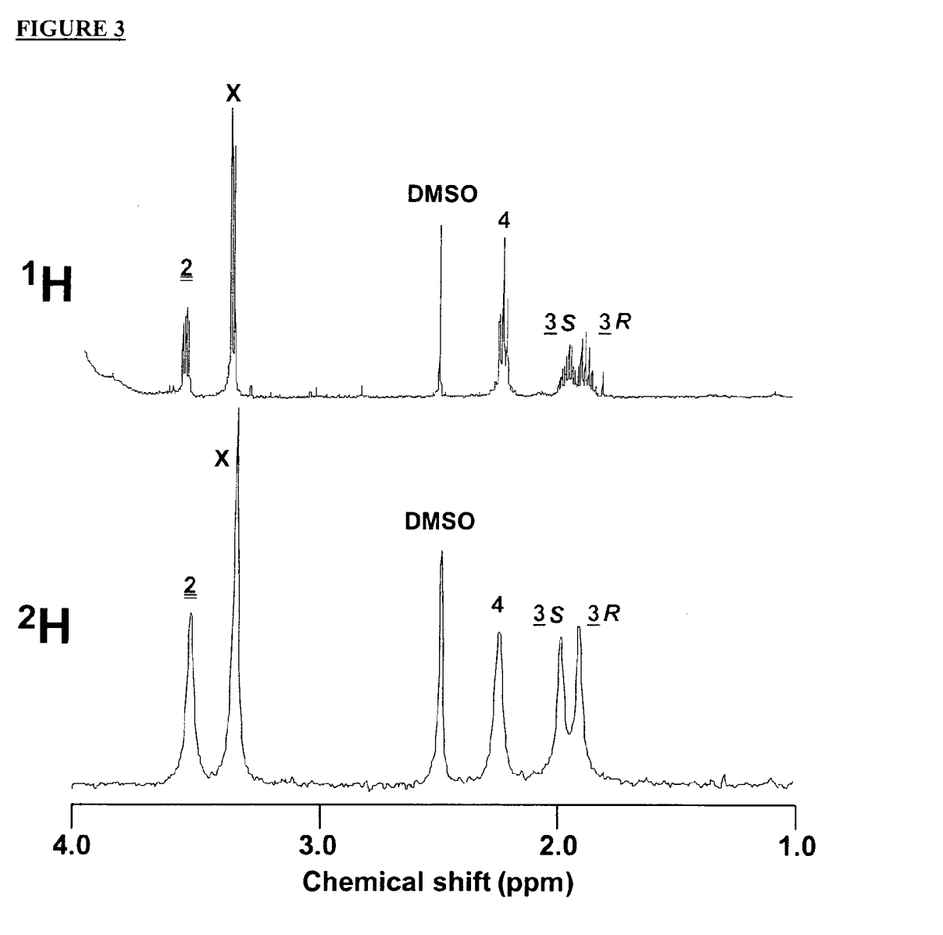
FIG. 3: illustrates $^1$H and $^2$H NMR spectra of glutamate obtained from the hydrolysis of urinary phenylacetylglutamine of an overnight fasted subject. Both spectra were processed with 0.5 Hz line-broadening. The $^1$H spectrum represents one acquisition while the $^2$H spectrum represents 7,608 free-induction decays. The number above each resonance identifies the positional aliphatic glutamyl hydrogen and the metabolic origin of each positional $^2$H-enrichment site as depicted in FIG. 1.

The inventors have found that glutamine derived by cataplerosis may be distinguished from glutamine derived from proteolysis when $^2H$ NMR traces are analysed. FIG. 3 illustrates how $^2H$ hydrogen atoms on the carbon backbone of glutamine can be resolved at positions 2, 3 or 4. The presence of $^2H$ hydrogen, particularly at position 3, may be quantified, for instance as described in Example 1, to provide the ratio of cataplerotic glutamine/proteolytic glutamine in a sample.

According to a preferred embodiment of the first or second aspects of the invention a urine sample is taken from a subject that has previously ingested $^2H_2O$ (to load cataplerotic glutamine with $^2H$) and an agent that promotes excretion of glutamine from the body (e.g aspartame, sodium phenylacetate or sodium phenylbutyrate). A urine sample is then collected from the subject. The sample is then processed (see below) and $^2H$ NMR is conducted on the processed sample to analyze the cataplerotic glutamine and proteolytic glutamine content of the sample.

It is most preferred that a urine sample containing PAGN is processed by utilising the following procedure:

(A) The urine may be concentrated (e.g. by rotary evaporation).
(B) The pH of the concentrate may be adjusted to about 7 (e.g. with NaOH).
(C) The sample may then be centrifuged, the precipitate removed and the pH of the supernatant adjusted to 1.5 (e.g. with HCl).
(D) The supernatant may be applied to a solid-phase extraction column and PAGN eluted with ethyl acetate.
(E) The collected PAGN may then be hydrolysed to liberate glutamate by dissolving the ethyl acetate in acid and heating at about 100° C.
(F) The resulting solution may then centrifuged and the supernatant mixed with water and the pH adjusted to 1.0 (e.g. by addition of HCl).
(G) The solution may then be passed through a cation-exchange resin. The column was washed with water and free glutamate eluted with a volatile base (e.g 2M $NH_4OH$).
(H) The solvent may then be evaporated to dryness and the residue containing glutamate dissolved in deuterium-depleted water before $^2H$ NMR analysis Most preferred methods are described in the Examples. These preferred methods may be easily adapted to include a test compound which is to be screened according to the third or fourth aspects of the invention.

The methods of the first or second aspect of the invention are useful in the clinical management of animals or humans. The inventors' data indicate that, in healthy postabsorptive subjects, about 50% of the carbon skeletons in the hepatic glutamine pool are derived from protein breakdown. However they have also demonstrated that this ratio may change in subjects suffering from a critical illness (e.g. suffering from significant burns, wounding, inflammation or immunological conditions). The methods of the invention enable a clinician to distinguish whether glutamine is being synthesized in the body by inappropriate catabolism of protein (leading to muscle wastage etc) or is derived from Krebs cycle intermediaries. This information can provide valuable insight for a clinician and enable him or her to make decisions (with regards to treatments or diet) that will help to manage a patient's condition.

The methods of the first or second aspect of the invention are particularly useful for monitoring patients in Intensive Care Units (ICU). ICU patients are prone to muscle wasting and such wasting can be a major influence on morbidity and mortality. The methods of the invention can be exploited to gain an early insight into muscle wasting by assaying for an increase in proteolytic glutamine. Early detection of muscle wasting allows a clinician to adjust the diet of the patient and thereby improve the health of the patient. This early detection also benefits the hospital because it allows improved nutrition of ICU patients; reducing the time a patient will spend in ICU; and thereby reduces costs.

The methods of the first and second aspects of the invention can also be exploited in cosmetic clinics (to monitor lean mass loss in weight loss treatments); in sports medicine (to monitor muscle wasting or growth in athletes); in general fitness regimens (to monitor muscle wasting or growth); and to monitor the usefulness if nutritional supplements such as amino acid supplements used to promote muscle growth.

BRIEF DESCRIPTION OF THE DRAWINGS

The present invention will now be described in more detail with reference to the Examples and the figures, which describe.

DETAILED DESCRIPTION

Example 1

1.1 Abstract

The inventors conducted tests to demonstrate the value of the methods according to the invention for distinguishing between cataplerotic and proteolytic glutamine in urine samples from human subjects. Analysis of glutamine positional $^2$H-enrichments from $^2$H$_2$O was conducted using NMR. Glutamine derived by cataplerosis was taken to be enriched in position 3 while glutamine derived from proteolysis was not.

$^2$H-enrichments of glutamine were quantified in eight healthy subjects by $^2$H NMR analysis of urinary phenylacetylglutamine following ingestion of $^2$H$_2$O to 0.49±0.03% body water enrichment and 0.3 grams of phenylbutyric acid. Enrichment of glutamine position 2 was 0.33±0.02%; 3R was 0.27±0.02%; 3S was 0.27±0.02% and the mean enrichment of the two position 4 hydrogens was 0.17±0.01%. The fraction of hepatic glutamine derived from cataplerosis was estimated from the ratio of position 3 to body water enrichment. By this analysis, 55±3% of hepatic glutamine was derived from cataplerosis and 45±3% from proteolysis. Hydrogen 2 enrichment was significantly higher than either 3R or 3S (p<0.05) indicating that a fraction of unlabeled glutamate precursor underwent exchange with α-ketoglutarate that was not associated with the Krebs cycle. Mean enrichment of position 4 hydrogens was 0.66±0.01 that of positions 3R,S indicating that the methyl hydrogens of the acetyl-CoA precursor of cataplerotic glutamine were 66±1% exchanged with body water protons. In conclusion, hepatic glutamine $^2$H-enrichment from $^2$H$_2$O reflects the contribution of cataplerotic and proteolytic sources and the extent to which acetyl-CoA hydrogens are exchanged with those of body water.

1.2 Materials and Methods 1.2.1 Human Studies

All studies were performed in accordance with a protocol approved by the University Hospital of Coimbra Ethics Committee following informed consent from each subject. Subjects began fasting at 20:00 following a standard dinner. During the night, each subject ingested 5.0 g/kg body-water of $^2$H$_2$O as a 35% solution in non-carbonated spring water (~350 ml total volume) divided into equal 2 portions: The first portion was given at 01:00 and the second portion was given at 03:00. For the remainder of the study, the subject drank water containing 0.5% $^2$H$_2$O to maintain body water enrichment. At 07:00 the subjects ingested a gelatin capsule containing 300 mg phenylbutyric acid. Urine was collected between 09:00 and 11:00.

1.2.2 Isolation and Processing of Urinary Phenylacetylglutamine

Urine was concentrated to 10-15 ml by rotary evaporation, the pH of the concentrate was adjusted to 7 with 5M NaOH and the sample was centrifuged. After removal of precipitate, the supernatant pH was adjusted to 1.5 with 2M HCl and applied to a 20 ml solid-phase extraction column (Isolute HM-N, Symta, S.A.L., Spain). PAGN was eluted with 80 ml ethyl acetate and the ethyl acetate was evaporated to dryness. For hydrolysis of PAGN to glutamate, the ethyl acetate extract was dissolved in 5 ml of 6M HCl and heated for 24 hours at 105° C. The solution was centrifuged and the supernatant mixed with ~35 ml water. The pH was raised to 1.0 by addition of 2M NH$_4$OH and the solution was passed through a 18 cm×1 cm column of Dowex 50X8-200-H$^+$ cation-exchange resin. The column was washed with 40 ml of water, glutamate was eluted with 40 ml of 2M NH$_4$OH and the solvent was evaporated to dryness. The same hydrolysis and purification procedure was applied to a set of [2,3,3,4,4-$^2$H$_5$]glutamine samples to generate [2,3,3,4,4-$^2$H$_5$]glutamate standards. For NMR spectroscopy, the residue containing glutamate was dissolved in ~0.6 ml of deuterium-depleted water containing a known amount of 0.505 deuterated dimethyl sulfoxide (DMSO) as an internal $^1$H and $^2$H concentration standard.

1.2.3 NMR Spectroscopy

Proton-decoupled $^2$H NMR spectra were acquired at 11.75 T with a Varian Unity 500 system equipped with a 5-mm broadband probe (Varian, Palo Alto, Calif.). Spectra were obtained at 60° C. without field-frequency lock with a 90 degree pulse angle, a sweep width of 10 ppm, an acquisition time of 2 seconds, and a pulse delay of 5 seconds. Between 1,500 and 7,600 free induction decays (f.i.d.) were acquired per sample for collection times of 3-15 hours. The summed f.i.d.'s were processed with 0.5-Hz line-broadening before Fourier transform. Fully relaxed $^1$H NMR spectra were obtained under the same conditions with pre-saturation of the water signal. A pulse width of 45 degrees, acquisition time of 3 seconds and a delay of 16 seconds were used. Each $^1$H spectrum was acquired with a single f.i.d. $^2$H-enrichment of urine water was analyzed by $^2$H NMR as previously described (Yang et al (1993) Anal. Biochem. 212 p 277-282). All NMR spectra were analyzed using the curve-fitting routine supplied with the NUTS PC-based NMR spectral analysis program (Acorn NMR Inc., Fremont Calif.).

1.2.4 Calculation of Positional Glutamate $^2$H-Enrichment

Given the known $^2$H-enrichment of the DMSO standard (0.505%) and assuming equal DMSO and glutamate proton equivalents (the DMSO $^1$H or $^2$H signal represents 6 equivalent proton or deuterium atoms per molecule), the $^2$H-enrichment of any glutamate signal is simply the DMSO enrichment multiplied by the ratio of DMSO and glutamate $^2$H-signal intensities. In the case of glutamate position 2 (G2), the enrichment would be equal to 0.505×$^2$H signal$_{G2}$/$^2$H signal$_{DMSO}$. To account for the unequal amounts of DMSO and glutamate molecules present in the sample, this expression is multiplied by the relative amounts of DMSO and glutamate, obtained from the ratio of DMSO and glutamate $_1$H NMR signals ($^1$H signal$_{DMSO}$/$^1$H signal$_{G2}$). Therefore, the percent enrichment of glutamate hydrogen 2 was calculated from the following equation.

$$\text{G2 Enrichment (\%)} = 0.505 \times (^2\text{Hsignal}_{G2}/^2\text{Hsignal}_{DMSO}) \times (^1\text{Hsignal}_{DMSO}/^1\text{Hsignal}_{G2})$$

The positional $^2$H-enrichments of the resolvable prochiral hydrogen 3 positions were quantified in the same manner. The hydrogen pair of glutamate position 4 (G4) are magnetically equivalent hence the G4 deuterium signal represents the summed $^2$H-enrichment at these two sites and the mean enrichment per position 4 hydrogen is represented by one-half of the G4 signal intensity as follows:

$$\text{G4 Enrichment (\%)} = 0.505 \times 0.5 \times (^2\text{Hsignal}_{G4}/^2\text{Hsignal}_{DMSO}) \times (^1\text{Hsignal}_{DMSO}/^1\text{Hsignal}_{G4})$$

1.3 Results

1.3.1 $^2$H NMR Analysis of Urinary PAGN.

Glutamate was recovered from urinary phenylacetyl-glutamine in quantities ranging from 170 to 500 μmol. For $^2$H NMR spectroscopy, optimal signal linewidths were obtained with glutamate amounts of 300 μmol or less (~0.5 M concentration for our sample volumes). There were no detectable levels of phenylbutyrylglutamine in the samples as determined by $^1$H NMR analysis of concentrated urine fractions.

Figure 2:
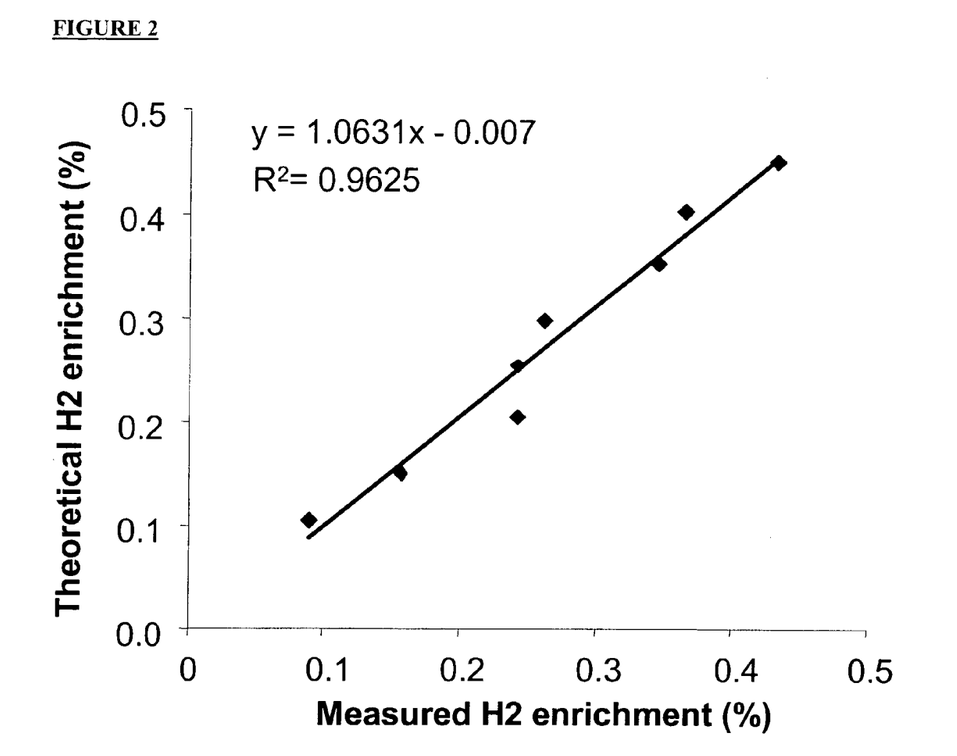
FIG. 2: illustrates the relationship between the theoretical and experimental $^2$H-enrichments of glutamate hydrogen 2 as measured by $^2$H NMR spectroscopy of a series of glutamate standards. The standards were prepared from glutamine precursors containing known fractions of [2,3,3,4,4-$^2$H$_5$] glutamine ranging from 0.1-0.5%.

Following desalting, acid hydrolysis and ion-exchange chromatography, the sample was characterized by $^1$H NMR signals of glutamate and an unknown metabolite with a resonance that was adjacent to the glutamate hydrogen 2 (labeled X in FIG. 3). For $^2$H NMR spectroscopy, optimal $^2$H-signal linewidths (~3 Hz) and dispersion were obtained by directly dissolving the glutamate eluted from the final cation-exchange column (essentially mono-ammonium glutamate) in water and acquiring the spectra at 60° C. Under these conditions, the hydrogen 3R and 3S signals are resolved, allowing the $^2$H-enrichment in each prochiral position to be determined. To check that the hydrolysis procedure did not alter the $^2$H-enrichment levels of the glutamyl hydrogens, a set of glutamine standards enriched with [2,3,3,4,4-$^2$H$_5$]glutamine were hydrolyzed and the resulting glutamate was purified by cation-exchange chromatography and analyzed by $^1$H and $^2$H NMR. The mean $^2$H signal ratios (relative to an arbitrary hydrogen 2 value of 100) were 100±3.3 (hydrogen 3R), 112±2.8 (hydrogen 3S) and 188±2.3 (hydrogen 4), which are all within ~10% of the theoretical 1:1:1:2 ratio. Moreover, the $^2$H-enrichment estimates for hydrogen 2 derived by NMR showed an excellent correlation with the real enrichment values as shown in FIG. 2. Enrichment of the other positions also were well correlated with the line of identity (hydrogen 3R; y=1.03x+0.01, R$^2$=0.97; hydrogen 3S; y=0.98x−0.02, R$^2$=0.93 and hydrogen 4; y=1.13x−0.01, R$^2$=0.96).

These data demonstrate that:
1) the positional $^2$H-enrichment distribution among the glutamine aliphatic hydrogens is preserved following purification and hydrolysis, and
2) the NMR method provides a precise and accurate measurement of absolute $^2$H-enrichment values.

FIG. 3 shows $^1$H and $^2$H NMR spectra of glutamate prepared from PAGN obtained from a healthy human subject who had previously ingested $^2$H$_2$O and phenylbutyric acid. The 1.5-4.0 ppm region of the spectrum that features the glutamate signals had an additional single resonance at 3.4 ppm from an unknown compound. The presence of both $^1$H and $^2$H NMR signals indicates that this site was enriched with $^2$H, consistent with a metabolite that underwent exchange with $^2$H-enriched body water and co-purified with PAGN and glutamate. The glutamate $^2$H signals derived from PAGN did not show an even distribution of $^2$H-enrichment, reflecting the specificity of exchange reactions that mediate the transfer of $^2$H from bulk water into the various positions of the glutamyl backbone hydrogens. The estimated fractional $^2$H-enrichments of each site, shown in Table 2, indicate that the position 2 hydrogen had the highest enrichment levels, followed by the hydrogen 3R and 3S sites, with the lowest enrichment values found for the position 4 hydrogens. The range of enrichments were substantially less that that of body water indicating that a significant fraction of hepatic glutamine molecules had not undergone exchange with $^2$H-body water and therefore could not have originated via the Krebs cycle but instead was derived from a metabolically inert glutamine pool.

TABLE 1

Positional $^2$H-enrichment of glutamate obtained from urinary phenylacetylglutamine for four healthy overnight fasted subjects given $^2$H$_2$O and phenylbutyrate during an overnight fast. Body water $^2$H-enrichment is also shown.

| Subject | PAGN Hydrogen 2 enrichment (%) | PAGN Hydrogen 3S enrichment (%) | PAGN Hydrogen 3R enrichment (%) | PAGN Hydrogen 4 enrichment (%) | Body water (%) |
|---|---|---|---|---|---|
| 1 | 0.25 | 0.20 | 0.21 | 0.14 | 0.47 |
| 2 | 0.44 | 0.39 | 0.42 | 0.25 | 0.67 |
| 3 | 0.35 | 0.25 | 0.25 | 0.16 | 0.51 |
| 4 | 0.35 | 0.27 | 0.27 | 0.17 | 0.57 |
| 5 | 0.32 | 0.23 | 0.23 | 0.16 | 0.40 |
| 6 | 0.30 | 0.26 | 0.24 | 0.18 | 0.42 |
| 7 | 0.32 | 0.30 | 0.29 | 0.19 | 0.41 |
| 8 | 0.28 | 0.23 | 0.23 | 0.15 | 0.44 |
| Mean | 0.33* | 0.27 | 0.27 | 0.17 | 0.49 |
| SEM | 0.02 | 0.02 | 0.02 | 0.01 | 0.03 |

*Significantly higher than H3S and H3R enrichments (p < 0.05, paired Student t-test)

TABLE 2

Sources of hepatic glutamine from the cataplerotic flux of the Krebs cycle and from proteolysis as estimated from the fractional $^2$H-enrichments in positions 2 and 3R,S relative to that of body water. Also shown is the fraction of proteolytic amino acids that participated in transaminase exchange before conversion to glutamine. By definition, glutamine molecules derived from the Krebs cycle will have complete incorporation of deuterium from body water into position 2 (i.e. equivalent to 100% exchange).

| | Glutamine carbon sources | | Exchange via transaminase | |
|---|---|---|---|---|
| ID | Krebs cycle | Proteolysis | Krebs cycle Sources | Proteolytic sources |
| 1 | 44 | 56 | 100 | 17 |
| 2 | 60 | 40 | 100 | 17 |
| 3 | 49 | 51 | 100 | 38 |
| 4 | 47 | 53 | 100 | 27 |
| 5 | 58 | 43 | 100 | 53 |
| 6 | 60 | 40 | 100 | 29 |
| 7 | 72 | 28 | 100 | 22 |
| 8 | 52 | 48 | 100 | 24 |
| Mean | 55 | 45 | 100 | 28 |
| SEM | 3 | 3 | | 4 |

1.4 Discussion 1.4.1 Analytical Considerations

The inventors have demonstrated that positional $^2$H-enrichment of human hepatic glutamine from $^2$H-enriched body water can be measured by $^2$H NMR following a relatively simple purification procedure.

In principle, the analysis can be directly applied to PAGN since this molecule has well resolved chemical shifts for the glutamyl backbone hydrogens. In practice, the inventors found it difficult to purify PAGN to a sufficient degree to avoid contamination from other urinary metabolites by simple SPE methods. In addition, a portion of PAGN can undergo isomerization to form phenylacetylisoglutamine during sample drying resulting in a mixture of the two compounds and dispersion of the NMR signals. Finally, with the use of phenylbutyric acid as the metabolite biopsy agent, there is always the possibility that phenylbutyrylglutamine could be produced in addition to PAGN, again potentially increasing the complexity of the NMR spectrum. Hydrolysis of SPE-purified PAGN (or phenylbutyrylglutamine) followed by isolation of the glutamate product by cation exchange greatly reduces background contributions from other urinary metabolites and generates a single analyte in good yield. Moreover, the recovered glutamate can be analyzed directly by NMR as an aqueous solution without need for pH adjustment or other manipulations aside from addition of the internal standard.

1.4.2 Intra-Versus Extrahepatic Sources of PAGN

Glutamine that is recruited for PAGN synthesis can originate from both hepatic and extrahepatic sources. There is evidence that the hepatic glutamine pool has a significant contribution from peripheral sources and is relatively well exchanged with plasma glutamine. Tracers that are extensively metabolized by skeletal muscle, such as [2-$^{14}$C]lactate, are recovered in glutamine that is sampled in the liver. With tracers that are preferentially metabolized by the hepatic Krebs cycle such as [U-$^{13}$C]propionate and [3-$^{14}$C]lactate, hepatic glutamine $^{13}$C-enrichment or $^{14}$C-specific activity is substantially less than that of other anaplerotic products such as glucose-6-phosphate. This is consistent with the dilution of labeled glutamine derived from the hepatic Krebs cycle by unlabeled glutamine from peripheral sources.

1.4.3 Glutamine $^2$H-Enrichment from $^2$H$_2$O

Figure 1:
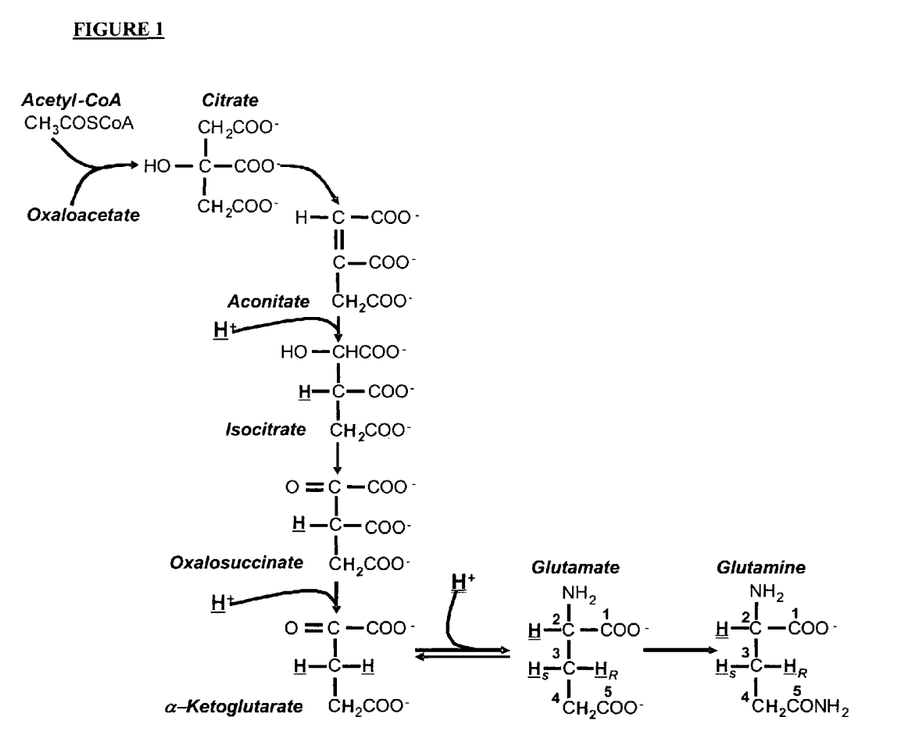
FIG. 1: Schematically illustrates sources of glutamine hydrogen enrichment from exchanges or addition of body water protons to Krebs cycle intermediates. The two hydrogen 4 atoms of glutamine (shown in bold) originate from the methyl hydrogens of acetyl-CoA. Hydrogen 3R (shown in bold and underlined) is incorporated from bulk water during the conversion of aconitate to isocitrate via aconitase and hydrogen 3S (also shown in bold and underlined) is incorporated during the conversion of oxalosuccinate to α-ketoglutarate via isocitrate dehydrogenase. Hydrogen 2 (shown in bold and double-underlined) is incorporated via the amination of α-ketoglutarate to glutamate by either transaminase or glutamate dehydrogenase.

FIG. 1 shows the metabolic steps that are involved in the transfer of $^2$H-enrichment from $^2$H-enriched body water into the five aliphatic hydrogens of glutamine. Enrichment of hydrogen 2 is achieved by the conversion of α-ketoglutarate to glutamate. This can be catalyzed by glutamate dehydrogenase, or alternatively, any transaminase that utilizes α-ketoglutarate as an amine receptor such as alanine aminotransferase or aspartate aminotransferase. In all cases, its is assumed that the incorporation of body water into position 2 is quantitative given the fact that there is essentially complete exchange between the precursor NADH hydrogen and that of bulk water (in the case of glutamate dehydrogenase) and the pyridoxal aldimine/ketimine intermediates and bulk water (in the case of transaminases). As a result, it can be assumed that $^2$H-enrichment level at position 2 reflects glutamine molecules that originated from α-ketoglutarate and from glutamate molecules that had participated in glutamate-α-ketoglutarate exchange.

For a glutamine molecule to be enriched in the position 3 hydrogens, its carbon skeleton needs to have originated from α-ketoglutarate that was generated from citrate either via the Krebs cycle or via cytosolic aconitase and isocitrate dehydrogenase. The 3R hydrogen is incorporated during the conversion of citrate to isocitrate, catalyzed by aconitase. The 3S hydrogen is incorporated following the conversion of isocitrate to α-ketoglutarate via proton addition to the transient oxalosuccinate intermediate. During a single turn of the Krebs cycle, both sites become enriched with body water resulting in equivalent enrichment of the 3R and 3S positions. While aconitase and isocitrate dehydrogenase activities are also present in the cytosol and could in principle result in enrichment of these sites independently of mitochondrial metabolism, the rapid equilibration of cytosolic and mitochondrial metabolite pools via citrate transport and malate-aspartate shuttles ensure that cytosolic and mitochondrial α-ketoglutarate pools are equivalently enriched from $^2$H-body water under steady-state conditions.

The carbon 4 position of a glutamyl moiety derived from the Krebs cycle originates from the methyl carbon of acetyl-CoA. The methyl hydrogens of acetyl-CoA have been shown to partially exchange with those of body water, as seen by the partial loss of deuterium following the metabolism of [2-$^{13}$C, 2-$^2$H$_3$]acetate to glutamate and glutamine. In addition, precursors of acetyl-CoA methyl hydrogens such as the methyl hydrogens of pyruvate are also extensively exchanged with those of body water. However, unlike the aconitase and isocitrate dehydrogenase reactions, the incorporation of body water hydrogens into the methyl site of acetyl-CoA and is not obligatory.

1.4.4 PAGN $^2$H-Enrichment Levels and Sources of Glutamyl Carbon Skeletons

In the context of enrichment from $^2$H-body water, the glutamyl moiety of PAGN can be considered to be derived from three distinct sources. These include:
1) the direct release of glutamine from protein breakdown;
2) amination of glutamate produced by protein breakdown (glutamate that is directly released in addition to glutamate produced from the catabolism of histidine, proline and asparagine); and
3) amination of a glutamate molecule derived from the Krebs cycle via cataplerosis.

Glutamine carbon skeletons derived from the Krebs cycle will be enriched in both 3R and 3S hydrogens whereas those derived from protein breakdown, be it in the form of glutamine or glutamate, will not be enriched in these sites. Therefore, the enrichment of glutamine 3R or 3S relative to that of body water is equivalent to the fraction of glutamine derived from the Krebs cycle. To the extent that protein-derived glutamine or glutamate undergoes exchange with α-ketoglutarate of the Krebs cycle, thus becoming enriched in position 3, the fraction of glutamine derived from the Krebs cycle will be overestimated and that from protein breakdown correspondingly undervalued. In this study, enrichment of the 3R,S sites relative to that of body water enrichment was ~55% indicating that half of the PAGN glutamyl moieties were derived from cataplerosis sources and the other half from protein breakdown. In a study of Kuhn et al. (1999) Am J. Clin. Nutr. 70 p 484-489) the rate of appearance of proteolytic glutamine was assessed by measuring the total protein turnover via [1-$^{13}$C]leucine and multiplying this by the fraction of protein glutamine residues. This rate represented ~14% of whole body glutamine $R_a$ indicating that proteolysis accounted for 14% and de novo synthesis accounted for 86% of glutamine $R_a$. In this analysis, de novo synthesis includes glutamine synthesized from both cataplerotic and proteolytic glutamate. Since the fraction of protein glutamate residues is ~4 times that of glutamine, the release of one equivalent of glutamine via proteolysis is accompanied by four of glutamate. If this glutamate is quantitatively converted to glutamine, it would account for ~56% of glutamine $R_a$. Therefore the maximal contribution of proteolytic carbon skeletons (glutamine+glutamate) to glutamine $R_a$ would be ~70%. The 45% contribution of these sources to PAGN as determined from the measurement of hydrogen 3/body water $^2$H-enrichment ratio may reflect the utilization of proteolytic glutamate by other pathways, and/or partial exchange of proteolytic glutamate with Krebs cycle metabolites.

Enrichment of glutamine position 2 originates during the conversion of α-ketoglutarate to glutamate and can be catalyzed by glutamate dehydrogenase and various transaminases that couple glutamate/α-ketoglutarate with other amino acids and their ketoacid equivalents. Therefore, glutamine molecules whose carbon skeletons are derived from the Krebs cycle will be enriched in this position as well as in position 3. The inventors' observation that position 2 enrichment was significantly higher than that of position 3 is best explained by the participation of unlabeled glutamate in transaminase exchange prior to being converted to glutamine. Moreover, this exchange must have involved α-ketoacid pools that were in isolation from Krebs cycle metabolites otherwise there would be no selective enrichment of position 2. The inventors therefore believe that the catalytic α-ketoacid pools associated with cytosolic transaminases might provide the opportunity for rapid glutamate/α-ketoglutarate exchange without mixing with α-ketoglutarate molecules derived from the Krebs cycle. From the difference in enrichment between positions 2 and 3 of hepatic glutamine, it is estimated that 23% of the proteolytic amino acid precursors participated in transaminase exchange before conversion to glutamine. Given that hydrogen 2 is enriched independently of cataplerotic Krebs cycle flux, its enrichment will overestimate the fraction of glutamine derived from cataplerosis.

1.4.5 Enrichment of Acetyl-CoA from $^2$H-Enriched Body Water

Carbon 4 of glutamate and its pair of hydrogens are derived from the methyl carbon and hydrogens of acetyl-CoA, a common product of pyruvate and fatty acid oxidation. Incorporation of acetyl-CoA into citrate via citrate synthase is accompanied by the loss of one of the methyl hydrogens. The remaining two hydrogens that are bound to the carbon do not participate in any of the reactions that transform citrate to glutamine. To the extent that these hydrogens do not exchange with those of body water during the conversion of citrate to α-ketoglutarate and glutamate, enrichment of position 4 reflects the enrichment of the acetyl-CoA molecules that entered the Krebs cycle. The extent of acetyl-CoA enrichment can be determined by comparing the relative enrichments of position 4 and position 3, since for every α-ketoglutarate molecule that is derived from the Krebs cycle, the position 3 hydrogens are fully exchanged with those of body water. From the PAGN positional enrichment levels presented in Table 1 the mean ratio of position 4 to position 3 $^2$H-enrichments was 0.66 indicating that exchange between the acetyl-CoA methyl hydrogens that fed the Krebs cycle and body water was 66% complete. This value may reflect a weighted contribution of acetyl-CoA from pyruvate, via pyruvate dehydrogenase, and from acyl sources including β-oxidation. The methyl hydrogens of acetyl-CoA derived from pyruvate are expected to be quantitatively exchanged with those of water as a result of alanine aminotransferase activity. For acetyl-CoA derived from β-oxidation of fatty acids, the extent of methyl hydrogen enrichment from $^2$H-body water is not known but is likely to be less than that of pyruvate. The β-oxidation sequence involves the incorporation of 2 water hydrogens per acetyl-CoA molecule released (hydration of trans-$\Delta^2$-enoyl-CoA by S-3-hydroxyacyl-CoA hydrolase and cleavage of acetyl CoA from 3-ketoacyl-CoA by 3-ketothiolase), giving a theoretical enrichment value of 66% that of body water. Exchanges via keto-enol tautomerism of β-oxidation intermediates may contribute additional enrichment. In the fasting state, β-oxidation accounts for the majority of acetyl-CoA production in liver and also the bulk of peripheral tissues, including skeletal muscle. Given this, it is likely that the bulk of PAGN position 4 hydrogens originated from β-oxidation with pyruvate oxidation supplying a minor fraction.

1.4.6 Whole-Body Glutamine Production and Hepatic Gluconeogenesis

For healthy, postabsorptive subjects, glutamine $R_a$ is 4.5-6.0 μmol/kg/min. In comparison, gluconeogenic flux is ~5.0 μmol/kg/min (10 μmol/kg/min of triose-P equivalents) of which 90%, or ~9 μmol/kg/min, is derived via the anaplerotic pathways of the Krebs cycle. Therefore, glutamine could potentially provide up to two thirds of anaplerotic carbons for gluconeogenesis. In healthy subjects infused with $^{13}$C-enriched glutamine, the contribution of glutamine to endogenous glucose production was estimated to be 8% after 18 hours of fasting rising to 16% after 42 hours of fasting. To the extent that the $^{13}$C-tracer is diluted as a result of exchanges at the level of the hepatic Krebs cycle and amino acid pools, these values likely underestimate the true contribution of glutamine to gluconeogenesis. Glutamine $R_a$ is significantly increased in several kinds of critical illness. In HIV-infected subjects, muscle wasting was associated with a ~50% increase in glutamine $R_a$. During sepsis, there is an increased efflux of glutamine from skeletal muscle which is associated with a net loss of protein. Critical illness is also characterized by hyperglycemia and increased gluconeogenic activity. In lung cancer patients experiencing loss of lean body mass, both endogenous glucose production and gluconeogenesis from alanine were significantly elevated compared to lung-cancer patients that were weight-stable. Insulin-resistant subjects who are not critically ill may also have an increased availability of amino acids for gluconeogenesis due to impaired stimulation of protein synthesis by insulin.

1.4.7 Concluding Remarks

These studies demonstrate that the methods of the first and second aspects of the invention may be exploited to provide useful information relating to the origins of glutamine an glutamate in subjects in a healthy or diseases state.

The data underlines the increased role of gluconeogenic amino acids derived from peripheral tissues on hepatic glucose metabolism in a range of disease conditions.

In conclusion, the methods of the invention present a simple and noninvasive method for resolving the contributions of whole-body metabolic and proteolytic activities to the supply of hepatic glutamine carbon skeletons based on the ingestion of $^2$H$_2$O and phenylbutyrate followed by the analysis of urinary PAGN. This analysis allows the role of peripheral intermediary metabolism and protein synthesis/degradation on the sources of hepatic glutamine carbons to be better defined. PAGN recovery and analysis can be integrated with $^2$H$_2$O measurements of hepatic gluconeogenesis. Therefore the methods of the invention allow for the relationship between hepatic glutamine sources and gluconeogenic activity to be explored in a variety of physiological and pathophysiological settings.

Example 2

The inventors conducted further experiments to demonstrate the usefulness of the methods of the invention.

The methods employed in Example 1 were exploited unless specified to the contrary.

Figure 4:
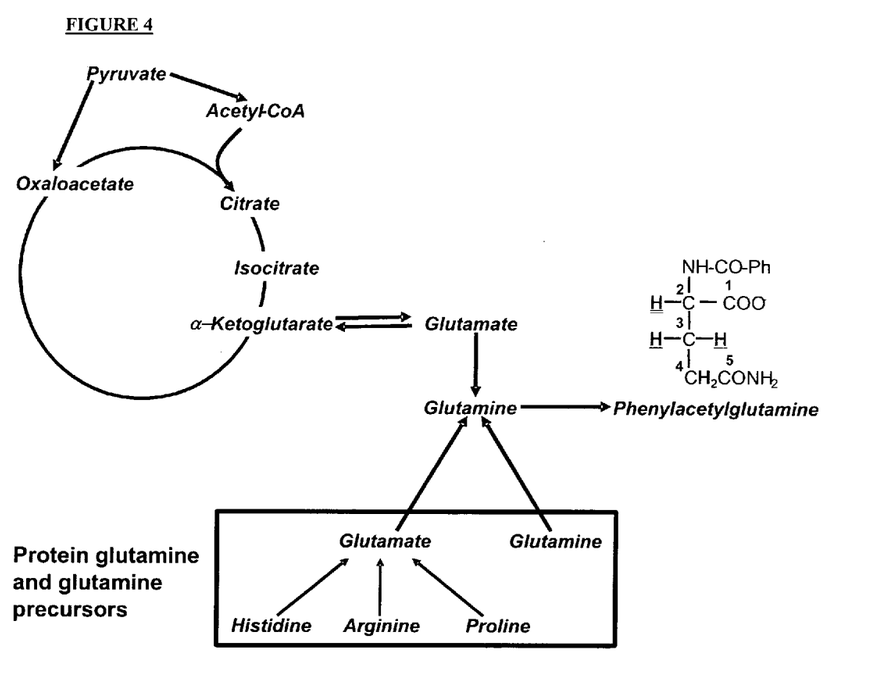
FIG. 4: Schematic model depicting the principal sources of the glutamine carbon skeleton of phenylacetylglutamine from the Krebs cycle and from protein amino acid residues. Also shown is the phenylacetylglutamine molecule with the glutamine aliphatic hydrogens highlighted in relation to their metabolic sources as depicted in FIG. 1.

Glutamine derived from peripheral tissues is an effective substrate for hepatic gluconeogenesis. Glutamine may be released during the proteolytic phase of protein turnover or it can originate from the Krebs cycle via cataplerosis (FIG. 4). To the extent that pathophysiological states such as insulin resistance modify whole-body protein kinetics, the availability of glutamine derived from proteolysis may be altered. Likewise, changes in peripheral tissue cataplerotic flux can also influence the availability of glutamine for hepatic gluconeogenesis. Whole-body glutamine availability can be determined by isotope dilution measurement but this method does not resolve the cataplerotic and proteolytic contributions.

The inventors resolved the cataplerotic and proteolytic contributions to hepatic glutamine by analysis of gln $^2$H-enrichment from $^2$H$_2$O. Glutamine derived from the Krebs cycle is enriched in the position 3 hydrogens (H3) while glutamine obtained via proteolysis, or synthesized from proteolytically-derived glutamate, is not enriched in these sites. Hence, the fraction of hepatic gln derived from cataplerotic sources is equal to H3 divided by body water enrichment (BW). Hepatic glutamine can be noninvasively sampled as urinary phenylacetylglutamine (PAGN) by ingestion of phenylbutyric acid.

Four healthy subjects ingested $^2$H$_2$O to 0.56±0.08% BW during overnight fasting. At 06:00, they took 300 mg phenylbutyric acid in a gelatin capsule. Urine was collected from 08:00-10:00 and BW was assayed directly by $^2$H NMR. Urinary PAGN was purified by solid phase extraction, hydrolyzed to glutamate, and analyzed by $^2$H NMR to obtain H3 enrichment values (as previously described). The percentage of hepatic gln derived from cataplerosis was estimated as 100×(H3/BW), with the balance being the proteolytic contribution. Data are presented as means±S.D.

From the glutamate $^2$H NMR spectra, H3 was estimated to be 0.29±0.09%. From the H3/BW ratio, the cataplerotic contribution to hepatic gln was 51±9% with proteolytic sources contributing 49±9%. Therefore in overnight-fasted healthy subjects, cataplerotic and proteolytic sources contribute equally to the hepatic glutamine pool.

The invention claimed is:

1. A method of distinguishing between glutamine formed by cataplerosis and glutamine formed by proteolysis in a subject, the method comprising:
   assaying a bodily sample from the subject for deuterated and non-deuterated glutamine by conducting $^2$H Nuclear Magnetic Resonance to quantify deuterated glutamine, the subject having had deuterated water administered to it between 2 and 24 hours before the sample is taken, and the subject having been treated with an agent that promotes excretion of glutamine from the subject; and
   determining a proportion of deuterated glutamine to total glutamine in the bodily sample and a proportion of non-deuterated glutamine to total glutamine in the bodily sample; and
   distinguishing between glutamine formed by cataplerosis and glutamine formed by proteolysis, wherein the proportion of deuterated glutamine to total glutamine is indicative of a proportion of glutamine formed from cataplerosis to total glutamine in the bodily sample and further wherein the proportion of non-deuterated glutamine to total glutamine is indicative of a proportion of glutamine formed from proteolysis to total glutamine.

2. The method according to claim 1 wherein the subject is a human being.

3. The method according to claim 1 wherein the bodily sample is a urine sample.

4. The method according claim 1 wherein the bodily sample is a urine sample and the agent promotes excretion of glutamine in urine.

5. The method according to claim 1 wherein the bodily sample is a urine sample and the agent promotes excretion of glutamine in urine and the agent includes a phenylacetyl moiety.

6. The method according to claim 1 wherein the bodily sample is a urine sample and the agent promotes excretion of glutamine in urine and the agent is one of: aspartame, sodium phenylacetate or sodium phenylbutyrate.

7. The method according to claim 1 wherein the bodily sample is a urine sample and the agent promotes excretion of glutamine in urine and wherein the agent and glutamine combine to form a phenylacetylglutamine (PAGN).

8. The method according to claim 7 wherein the urine sample is further processed to liberate glutamine or glutamate.

9. The method of claim 1 further comprising the step of evaluating the health status of a subject.

10. The method of claim 9 wherein the subject is suspected of having a critical illness which is at least partially characterized by increased proteolysis.

11. The method of claim 9 wherein the subject has, or is suspected of developing, muscle wasting.

12. The method of claim 9 wherein the subject is suspected of having an illness which is at least partially characterized by abnormal cataplerosis.

13. The method according to claim 1 wherein the bodily sample is a urine sample, the agent promotes excretion of glutamine in urine and includes a phenylacetyl moiety and wherein the agent and glutamine combine to form a phenylacetylglutamine (PAGN).

14. The method according to claim 13 wherein the urine sample is further processed to liberate glutamine or glutamate.

15. A method of distinguishing between glutamine formed by cataplerosis and glutamine formed by proteolysis in a subject, the method comprising:

administering, to the subject, deuterated water and an agent that promotes excretion of glutamine from the subject;

obtaining a bodily sample from the subject between 2 and 24 hours after the administration of deuterated water; and quantifying an amount of deuterated glutamine and an amount of non-deuterated glutamine in the bodily sample, and determining a proportion of deuterated glutamine to total glutamine in the bodily sample and a proportion of non-deuterated glutamine to total glutamine in the bodily sample; and distinguishing between glutamine formed by cataplerosis and glutamine formed by proteolysis in the subject, wherein the proportion of deuterated glutamine to total glutamine indicates a proportion of glutamine formed from cataplerosis to total glutamine in the bodily sample and the proportion of non-deuterated glutamine to total glutamine is indicative of a proportion of glutamine formed from proteolysis to total glutamine in the bodily sample.

* * * * *